United States Patent
Mehta et al.

(10) Patent No.: US 10,345,295 B2
(45) Date of Patent: Jul. 9, 2019

(54) DEVICE AND METHOD FOR POINT-OF-CARE DIAGNOSTICS AND ANTIBIOTIC RESISTANCE IDENTIFICATION, AND APPLICATIONS THEREOF

(71) Applicant: CORNELL UNIVERSITY, Ithaca, NY (US)

(72) Inventors: Saurabh Mehta, Ithaca, NY (US); David Erickson, Ithaca, NY (US); Seoho Lee, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 15/875,686

(22) Filed: Jan. 19, 2018

(65) Prior Publication Data

US 2018/0196041 A1    Jul. 12, 2018

Related U.S. Application Data

(63) Continuation-in-part of application No. PCT/US2016/043102, filed on Jul. 20, 2016, which is a continuation of application No. 62/194,389, filed on Jul. 20, 2015.

(51) Int. Cl.
*G01N 33/543* (2006.01)
*G01N 33/558* (2006.01)
(Continued)

(52) U.S. Cl.
CPC ...... *G01N 33/54366* (2013.01); *B01L 3/5023* (2013.01); *B01L 3/502715* (2013.01);
(Continued)

(58) Field of Classification Search
CPC ............ G01N 33/54366; G01N 33/558; B01L 3/5023; B01L 3/502715; C12Q 1/18
See application file for complete search history.

(56) References Cited

U.S. PATENT DOCUMENTS 5,053,199 A * 10/1991 Keiser .............. G01N 35/00594
422/68.1
5,195,023 A *  3/1993 Manzione ................ H05K 7/00
257/629

(Continued)

OTHER PUBLICATIONS

Hart, R. W. et al., Oral Diseases, 2011, vol. 17, pp. 745-752.
(Continued)

*Primary Examiner* — Melanie Brown
(74) *Attorney, Agent, or Firm* — Bond, Schoeneck & King, PLLC; Blaine Bettinger

(57) ABSTRACT

A device for detecting the presence of a target in a sample including a first port configured to receive a multi-layered substrate having a sample inlet and a reagent inlet. The sample inlet is connected to a first microfluidic channel and the reagent inlet is connected to both the first microfluidic channel and a second microfluidic channel. The second microfluidic channel has a longer pathway than the first microfluidic channel. A first test strip and a second test strip are each connected to both the first microfluidic channel and the second microfluidic channel, while a third test strip is connected only to the first microfluidic channel. Each test strip includes a conjugate section, a detection section, and a collection section.

13 Claims, 16 Drawing Sheets

(51) Int. Cl.
*B01L 3/00* (2006.01)
*C12Q 1/18* (2006.01)
(52) U.S. Cl.
CPC ............. *C12Q 1/18* (2013.01); *G01N 33/558* (2013.01); *B01L 2200/027* (2013.01); *B01L 2300/0663* (2013.01); *B01L 2300/0816* (2013.01); *B01L 2300/0864* (2013.01); *B01L 2300/0883* (2013.01); *B01L 2300/0887* (2013.01); *G01N 2333/4737* (2013.01); *G01N 2333/5753* (2013.01); *G01N 2800/26* (2013.01)

(56) References Cited

U.S. PATENT DOCUMENTS

| 8,697,007 | B2 | 4/2014 | Bau et al. |
| 9,133,498 | B2 | 9/2015 | Kwon et al. |
| 2003/0119202 | A1* | 6/2003 | Kaylor ............... G01N 21/8483 436/514 |
| 2009/0325276 | A1 | 12/2009 | Battrell et al. |

OTHER PUBLICATIONS

Cira, Nate J. et al., Lab on a chip, 2012, vol. 12, pp. 1052-1059.
International Search Report and Written Opinion dated Oct. 12, 2016, PCT/ISA/210, 6 pages.

* cited by examiner

DEVICE AND METHOD FOR POINT-OF-CARE DIAGNOSTICS AND ANTIBIOTIC RESISTANCE IDENTIFICATION, AND APPLICATIONS THEREOF

CROSS-REFERENCE TO RELATED APPLICATIONS

The present application claims priority to under 35 U.S.C. § 111(a) to PCT/US2016/043102 filed Jul. 20, 2016, which claims the benefit of U.S. Provisional Application No. 62/194,389, filed on Jul. 20, 2015, the entire contents of which are hereby incorporated by reference in their entireties.

FIELD OF THE INVENTION

The present disclosure is directed generally to a device for molecular diagnostics, and more particularly, to a portable device with a three-stage test immunoassay and minimum inhibitory concentration assay for point-of-care diagnosis.

BACKGROUND

Currently, sepsis at different life stages, neonatal, childhood, or in adults, is a leading cause of death globally. Neonatal sepsis, in particular, presents vague signs and symptoms; therefore, current management of neonatal sepsis requires a high index of suspicion, even on the part of highly trained clinicians. For example, one presenting sign may only include an alteration in feeding behavior. Further, the use of antibiotics must be carefully calculated as the inappropriate use of antibiotics leads to the emergence of resistant strains of pathogens.

The sustained increase in antibiotic resistance (ABR) is a major concern worldwide that is affecting patient outcomes causing significant increases in morbidity and mortality. As per the 2015 World Health Organization (WHO) report on current practices in place to address ABR, many governments have initiatives, but there are major discontinuities in action across all 6 WHO regions and many low-income countries do not have a response plan. A recent review has estimated 10 million deaths worldwide and economic loss of around $100 trillion due to drug-resistant infections. The Centers for Disease Control and Prevention (CDC) reports that almost 50% of antibiotics prescribed for people are not required and also not effective. Additionally, the CDC reports that each year in the U.S., at least 2 million people acquire bacterial infections resistant to one or more antibiotics and at least 23,000 people die each year as a result.

Traditional minimum inhibitory concentration (MIC) assays are performed by diffusion or dilution methods. Diffusion method involves a hydrophilic strip or disc infused with antibiotic that is placed in contact with the agar plate surface on which a microbe is cultured. The MIC is estimated based on a visual 'zone of inhibition' around the disc or strip. The analyses of results obtained by diffusion method are subjective and variable. In dilution method, a series of culture tubes or agar plates with nutrient media and serial dilution of an antibiotic are used to grow bacteria. The MIC is determined by visual inspection, by identifying the lowest concentration of antibiotics that inhibits bacterial growth. The guidelines for determining MIC by dilution-based methods have been published by the Clinical Laboratory and Standards Institute (CLSI) in the U.S.

The majority of quantitative ABR evaluation is done via automated systems that are not portable and rely on some variant of traditional microdilution testing. Conceptually, in these systems, the bacterial sample is split and exposed to an array of different antibiotics and doses. The plate or card is incubated for a period of time and then read to determine the MIC of each antibiotic that halts cell growth. The specifics of the assay and their read out format vary from manufacturer to manufacturer (see the Vitek II, Brilliance™ ESBL, MicroScan WalkAway, Phoenix, and Sensititre systems), but generally require at least 16 to 24 hours for obtaining final susceptibility results depending on the organism.

Several microfluidic implementations of diffusion/dilution methods have been reported to reduce assay time and rely on applying plugs of fluids, concentration gradient generators, microparticles and dielectrophoresis. However, these approaches require multiple steps, technician training and other external equipment such as syringe pump, which are barriers to translating these devices to clinical applications and point-of-care diagnostics. There is a need for a point-of-care MIC assay technology that does not require external equipment, can be operated without extensive user training, and can measure the MIC of various antibiotics with required specificity/sensitivity in a cost-effective manner.

Technological advancements, especially in the medical field, seldom reach resource-limited populations. For example, current medical diagnostic equipment can be costly, bulky, and require sophisticated training to operate and maintain. Therefore, there is a need in the art for a point-of-care molecular diagnostic device that can identify infectious disease pathogens and antibiotic resistance quickly and with little skill required such to enable health workers around the globe appropriately refer and manage infections and sepsis.

Description of the Related Art Section Disclaimer: To the extent that specific patents/publications/products are discussed above in this Description of the Related Art Section or elsewhere in this Application, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

SUMMARY OF THE INVENTION

Embodiments of the present invention recognize that there are potential problems and/or disadvantages with the conventional devices for molecular diagnostics. Therefore, the need exists for a simple-to-use device which can identify pathogens and their resistance to antibiotics at the point-of-care. Various embodiments of the present invention may be advantageous in that they may solve or reduce one or more of the potential problems and/or disadvantages discussed herein.

The present disclosure is directed to an inventive configuration, structure, and resulting function of a device for detecting the presence of a target in a sample. The device comprises a first port configured to receive a multi-layered substrate having a sample inlet and a reagent inlet. The sample inlet is connected to a first microfluidic channel and the reagent inlet is connected to both the first microfluidic channel and a second microfluidic channel. The second microfluidic channel comprises a longer pathway than the first microfluidic channel. A first test strip and a second test strip are each connected to both the first microfluidic channel and the second microfluidic channel, while a third test strip is connected only to the first microfluidic channel. Each test strip comprises a conjugate section, a detection section, and a collection section.

According to an alternative embodiment, a method for detecting a target in a sample comprises the step of first providing a device having a first port configured to receive a multi-layered substrate having a sample inlet and a reagent inlet. The sample inlet is connected to a first microfluidic channel and the reagent inlet is connected to both the first microfluidic channel and a second microfluidic channel. The second microfluidic channel comprises a longer pathway than the first microfluidic channel. A first test strip and a second test strip are each connected to both the first microfluidic channel and the second microfluidic channel, while a third test strip is connected only to the first microfluidic channel. Each test strip comprises a conjugate section, a detection section, and a collection section. Once the device is provided, the method further comprises the steps of labeling detection antibodies of the target with nanoparticles and depositing the detection antibodies at the conjugate section. Secondary antibodies of the target are also labeled with nanoparticles and deposited at the conjugate section. Next, the sample is inserted into the sample inlet and a reagent is inserted into the reagent inlet. At the next step, the sample flows across each test strip. Finally, detection antibodies and secondary antibodies are captured at the detection section.

According to another embodiment, a method for detecting a target in a sample comprises the step of first providing a device having a first port configured to receive a multi-layered substrate having a sample inlet and a reagent inlet. The sample inlet is connected to a first microfluidic channel and the reagent inlet is connected to both the first microfluidic channel and a second microfluidic channel. The second microfluidic channel comprises a longer pathway than the first microfluidic channel. A first test strip and a second test strip are each connected to both the first microfluidic channel and the second microfluidic channel, while a third test strip is connected only to the first microfluidic channel. Each test strip comprises a conjugate section, a detection section, and a collection section. The device comprises a second port configured to receive a MIC chip interface. The MIC chip interface has an open volume configured to receive a MIC chip therein. The MIC chip comprises one or more wells and the MIC chip interface comprises one or more magnets in alignment with the wells when the MIC chip is inserted into the open volume of the MIC chip interface. Once the device is provided, the method further comprises the steps of applying an antibiotic to a solid media in each well, inserting the MIC chip into the MIC chip interface, mixing a sample with a biorecognition element to create a mixture, depositing the mixture into the MIC chip, and flowing the mixture across the wells.

BRIEF DESCRIPTION OF THE DRAWINGS

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments.

Reference is now made briefly to the accompanying drawings, in which.

Figure 1:
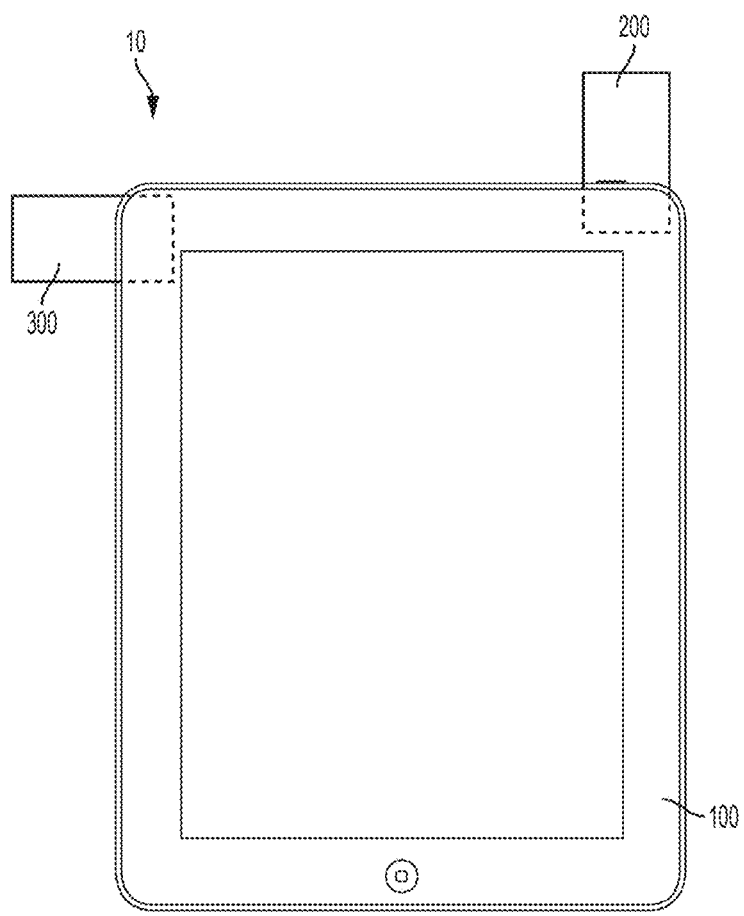
FIG. 1 is a perspective view schematic representation of an exemplary embodiment of a device to detect the presence of a target in a sample.

Where applicable, like reference characters designate identical or corresponding components and units throughout the several views, which are not to scale unless otherwise indicated. Moreover, the embodiments disclosed herein may include elements that appear in one or more of the several views of in combinations of the several views.

DETAILED DESCRIPTION OF EMBODIMENTS

Referring now to the drawings, wherein like reference numerals refer to like parts throughout, there is seen in FIG. 1 a perspective view schematic representation of an exemplary embodiment of a device 100 to detect the presence of a target in a sample. The device 100 is part of a system 10 that can include a first port configured to receive a fluid network 200 and a second port configured to receive a minimum inhibitory concentration (MIC) chip assembly 300. In use, the system 10 can identify infectious disease pathogens and determine antibiotic resistance. Examples of targets identified by the system include, but are not limited to C-Reactive Protein (CRP), procalcitonin (PCT), and Endotoxin. In one embodiment, the device 100 is an electronic device, such as a smartphone, for example. As smartphones are becoming increasingly ubiquitous and user-friendly, they provide a compact platform that can transform health care.

Figure 2:
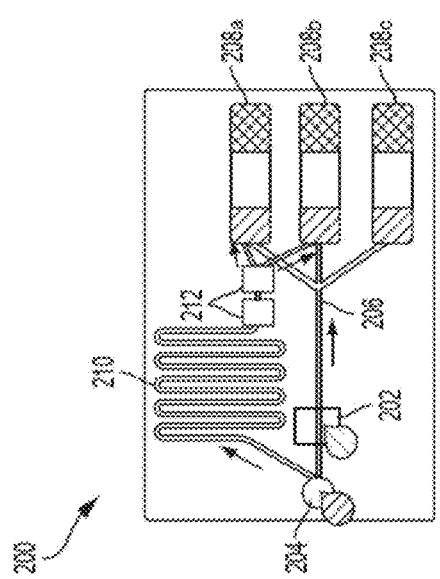
FIG. 2 is a perspective view schematic representation of an exemplary embodiment of the fluid network of the device.

Referring now to FIG. 2, there is shown a perspective view schematic representation of an exemplary embodiment of the fluid network 200 of the device 100. In the embodiment shown in FIG. 2, the fluid network 200 comprises a substrate having a sample inlet 202 and a reagent inlet 204. The sample inlet 202 is configured to receive a sample, such as a drop of blood and the reagent inlet 204 is configured to receive a reagent, such as a buffer. The sample inlet 202 may additionally comprise a filtration membrane to maintain the sample before the flow of the sample is initiated.

The sample inlet 202 is connected to a first microfluidic channel 206. The first microfluidic channel 206 extends to a first test strip 208a, a second test strip 208b, and a third test strip 208c. The reagent inlet 204 is connected to the first microfluidic channel 206 and is also connected to a second microfluidic channel 210. The second microfluidic channel 210 connects only to the first test strip 208a and the second test strip 208b. In the depicted embodiment, the sample inlet 202 is disposed in the first microfluidic channel 206 between the reagent inlet 204 and the test strips 208a-c. When a sample is inserted into the sample inlet 202, the sample remains in a filtration membrane of the sample inlet 202 until contacted by the reagent. Thus, application of the reagent via the reagent inlet 204 initiates flow of the sample to the all three test strips 208a-c.

The application of a reagent via the reagent inlet 204 also initiates flow of the reagent into the second microfluidic channel 210, which comprises an enhancement solution membrane 212 therein. The enhancement solution membrane 212 contains an enhancement solution used to amplify the detection of the target in the sample as some targets are found in very low concentrations. For example, PCT and Endotoxin are found in very low concentrations (pg/ml-ng/ml) in blood. Thus, the enhancement solution would permit detection of low concentrations of PCT and Endotoxin that would otherwise be difficult or impossible to detect. In one embodiment, the enhancement solution is a silver enhancement solution.

The second microfluidic channel 210 comprises a longer pathway than the first microfluidic channel 206. For example, in the embodiment shown in FIG. 2, the second microfluidic channel 210 is tortuous thereby creating a longer pathway than the first microfluidic channel 206. However, other pathway configurations are contemplated. When a reagent is applied via the reagent inlet 204, the reagent must travel the longer pathway in the second microfluidic channel 210 before it contacts the enhancement solution membrane 212. Once the reagent reaches the enhancement solution membrane 212, the enhancement solution is released and flows in the second microfluidic channel 210 to the first test strip 208a and the second test strip 208b.

As described above and shown in FIG. 2, the tortuous second microfluidic channel 210 comprises a longer pathway creating a time delay from the time the sample reaches the test strips 208a-c to the time the enhancement solution reaches the first test strip 208a and the second test strip 208b. The time delay created by the longer pathway of the second microfluidic channel 210 allows optimal exposure of the first test strip 208a and the second test strip 208b to the sample before the enhancement solution is introduced.

Figure 3:
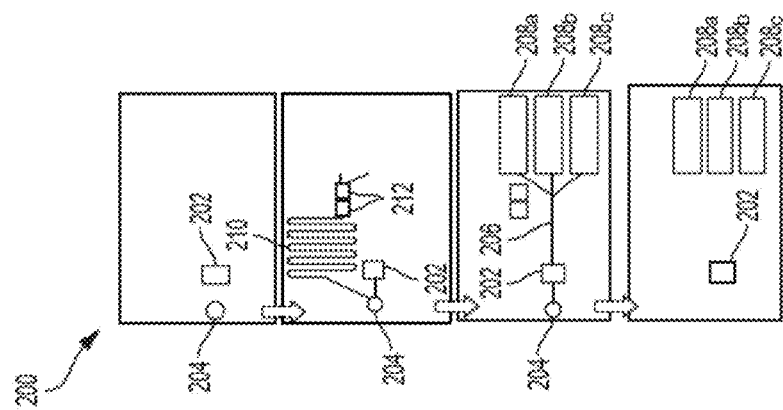
FIG. 3 is a structure diagram of an exemplary embodiment of the fluid network of the device.

A structure diagram of an exemplary embodiment of the fluid network 200 is shown in FIG. 3. The embodiment of the fluid network 200 shown in FIG. 3 is composed of a substrate having a four-layer structure. As shown in FIG. 3, the first microfluidic channel 206 and the second microfluidic channel 210 extend through different layers of the substrate to allow for optimal flow in a compact structure. The substrate may be composed of a plastic composition or other like materials.

In the embodiments shown in FIGS. 2-3, there are three test strips 208a, 208b, 208c, which may detect Endotoxin, PCT, and CRP, respectively. The three-plex test configuration provides rapid detection and identification of pathogens known to cause or otherwise contribute to neonatal sepsis. As stated above, PCT and Endotoxin are found in very low concentrations in the blood. Thus, in the embodiments shown in FIGS. 2-3, test strips representing an Endotoxin test strip 208a and a PCT test strip 208b are connected to both the second microfluidic channel 210 and the first microfluidic channel 206. This configuration allows the Endotoxin test strip 208a and the PCT test strip 208b to receive and be exposed to the sample before the enhancement solution arrives from the second microfluidic channel 210. However, as CRP is found in higher concentrations in the blood and thus does not require the enhancement solution, the CRP test strip 208c is only connected to the first microfluidic channel 206. Other configurations are contemplated for specific targets and combinations of targets.

Figure 4:
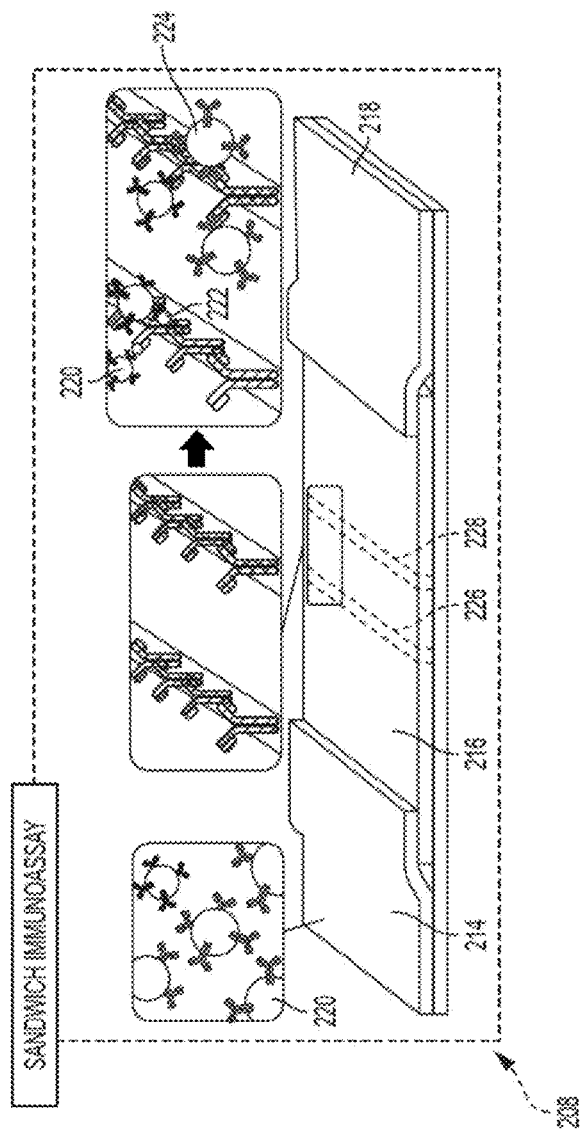
FIG. 4 is a perspective view schematic representation of an exemplary embodiment of a test strip of the fluid network.

Referring now to FIG. 4, there is shown a perspective view schematic representation of an exemplary embodiment of a test strip 208a-c of the fluid network 200. Each test strip may comprise a plurality of sections. In the embodiment shown in FIG. 4, the test strip 208a-c comprises three sections: a conjugate section 214, a detection section 216, and a collection section 218. In the depicted embodiment, the sections are contiguous, with the detection section 216 between the conjugate section 214 and the collection section 218. Such a configuration creates test strips 208a-c according to sandwich-type lateral flow principles.

The conjugate section 214 may store detection antibodies 220. In one embodiment, the detection antibodies are labeled with gold nanoparticles. The detection section 216 captures and immobilizes the detection antibodies 220 for the target molecules 222 only if the target molecules 222 are present. The detection section 216 captures detection antibodies 220 because it is composed of nitrocellulose or similar material that has a high protein-binding affinity. Captured detection antibodies 220 may include, but are not limited to, anti-CRP, anti-PCT, and anti-Endotoxin. The collection section 218 immobilizes secondary antibodies 224 with an affinity for the common species of the detection antibodies 220. The common species may include a mouse, rabbit, goat and the like. The secondary antibodies 224 are similarly captured by the detection section 216 if the target molecules 222 are present.

As the lateral flow assay is conducted, the detection section 216 captures the detection antibodies 220 and the secondary antibodies 224 as a test line 226 and a control line 228, respectively. The test line 226 changes color when detection antibodies 220 are captured, indicating that target molecules are present in the sample. For example, the test line 226 may turn a reddish color when the detection antibodies 220 are captured at the detection section 216. The color change of the test line 226 may be more vibrant and conspicuous when a high concentration of target molecules are present in the sample. Similarly, when a low concentration of target molecules are present in the sample, the color change may be more subtle. Determining the concentration of target molecules in a sample at the point-of-care is critical as concentrations of target molecules are correlated to certain types of diseases. For example, CRP levels of 1-6 µg/ml can be an indication of heart disease risk, while CRP levels greater than 10 µg/ml indicate inflammation, either from infection or other inflammatory diseases.

Figure 5:
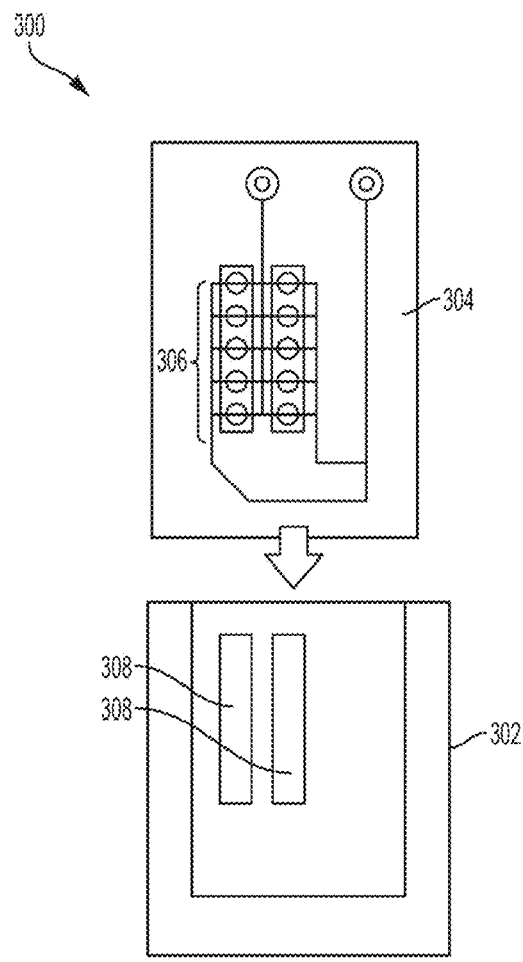
FIG. 5 is a perspective view schematic representation of an exemplary embodiment of the minimum inhibitory concentration (MIC) chip assembly of the device.

Referring now to FIG. 5, there is shown a perspective view schematic representation of an exemplary embodiment of the minimum inhibitory concentration (MIC) chip assembly 300 of the device 100. The MIC chip assembly 300 comprises a MIC chip interface 302 having an open volume configured to receive a MIC chip 304 therein. In the embodiment shown in FIG. 5, the MIC chip interface 302 slidably receives the MIC chip 304. The MIC chip 304 comprises one or more wells 306 configured to receive a sample. The MIC chip interface 302 comprises one or more magnets 308 that align with the wells 306 when the MIC chip interface 302 receives the MIC chip 304. In the embodiment shown in FIG. 5, the wells 306 may be arranged into an array for optimal alignment with the magnets 308.

Figure 6:
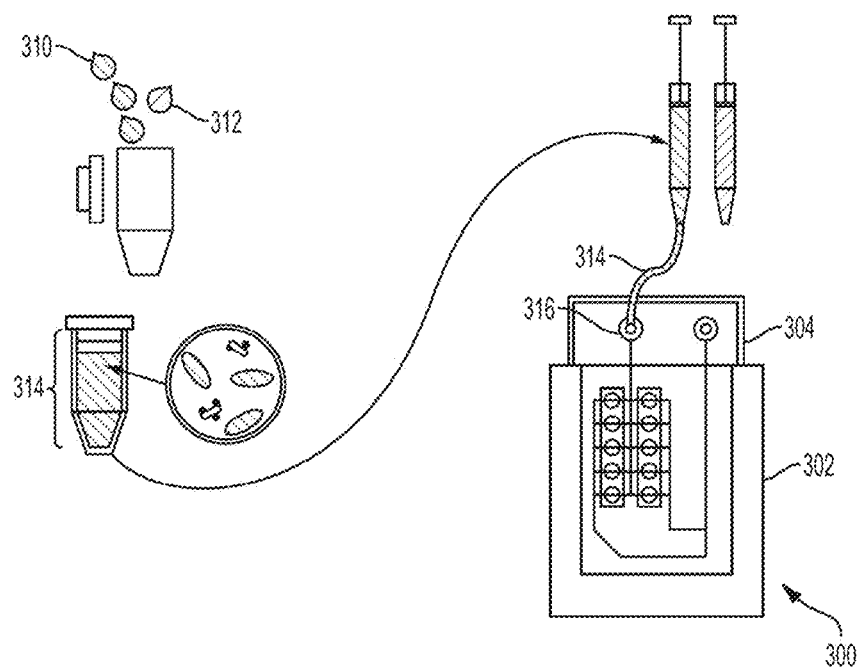
FIG. 6 is a perspective view schematic representation of an exemplary embodiment of a sample mixture inserted into the MIC chip.

Referring now to FIG. 6, there is shown a perspective view schematic representation of an exemplary embodiment of a sample mixture inserted into the MIC chip. In the embodiment shown in FIG. 6, a sample 310 is mixed with a biorecognition element 312. The sample 310 can be a biological sample, such as a blood sample. In one embodiment, the biorecognition element 312 is a magnetic nanoparticle. Magnetic nanoparticles can be functionalized with capture ligands specific to bacterial organisms. Thus, when a sample is mixed with functionalized magnetic nanoparticles, the nanoparticles attach to the specified bacterial organisms in the sample. As shown in FIG. 6, the sample 310 and the biorecognition element 312 are combined to create a mixture 314, such as a blood magnetic nanoparticle mixture. The mixture 314 is then inserted into an inlet 316 on the MIC chip 304.

Figure 7:
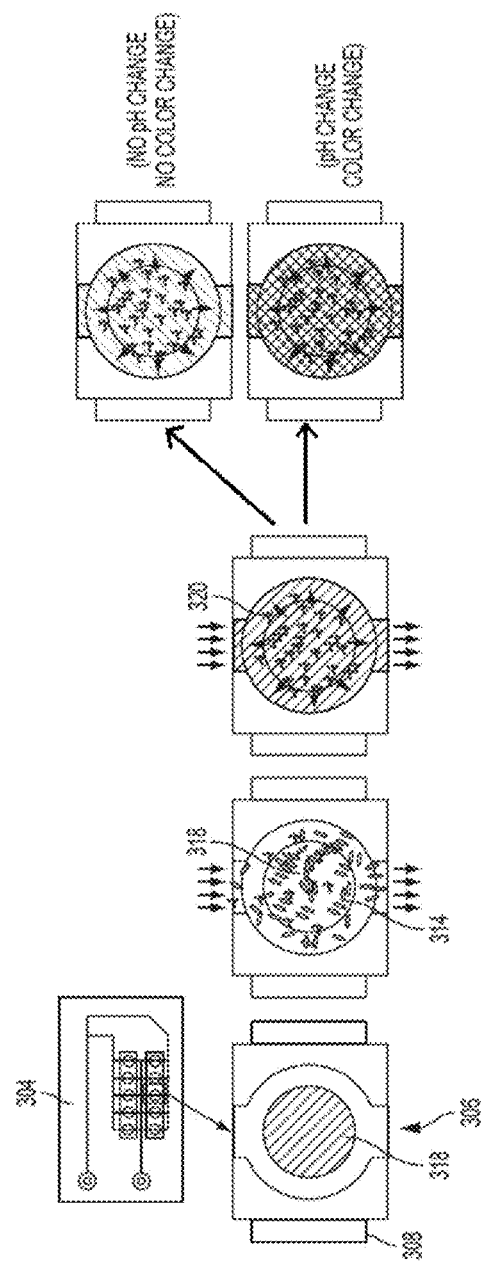
FIG. 7 is a diagram of an exemplary embodiment of a well during a MIC assay.

Referring now to FIG. 7, there is shown a diagram of an exemplary embodiment of a well during the MIC assay. In the embodiment shown in FIG. 7, each well is pre-functionalized with specific varying concentrations of an antibiotic within a solid media 318. For example, the solid media 318 may be doped agar, although numerous other like materials can be used. Once the MIC chip 304 is inserted into the MIC chip interface 302 and the wells 306 align with the magnets 308, the mixture 314 is flown through the MIC chip 304 such that it is evenly distributed to each of the wells 306. The magnets 308 attract the magnetic nanoparticles, thereby collecting bacterial organisms attached to the magnetic nanoparticles in the mixture 314 while the remainder of the mixture 314 flows through the wells 306.

In some embodiments, a culture medium with an indicator is inserted into the inlet 316 on the MIC chip 304. The indicator washes the remainder of the mixture 314 from the wells 306. It also introduces growth or culture medium, if necessary, and a chemical indicator. A chemical indicator can be any compound or solution that indicates whether an organism is alive, dead, or metabolically, or otherwise, active. An example of a chemical indicator is phenol red, which will change the color of a solution in the presence of metabolically active organisms due to the changes in pH of the solution caused by the metabolic activity changes occurring in the organisms.

After the mixture 314 and culture medium with a chemical indicator has been added, antibiotic 320 begins to diffuse from the solid media 318. If the organisms captured in the solid media 318 are not resistant to the antibiotic 320, the organisms will not experience metabolic activity changes that trigger a change in pH of the solution in the well 306. However, if the organisms thrive despite the antibiotic 320, the organism experience metabolic activity changes that alter the pH of the solution in the well 306. As the pH of the solution decreases and becomes more acidic, the chemical indicator changes the color of the solution. Thus, the wells 306 comprising organisms which are resistant to the antibiotic 320, will have a different color, or other indication, than wells 306 comprising organisms which are not resistant to the antibiotic 320. Further, as each well 306 in the array comprises a different concentration of antibiotic 320, a minimum inhibitory concentration can be ascertained.

Figure 8:
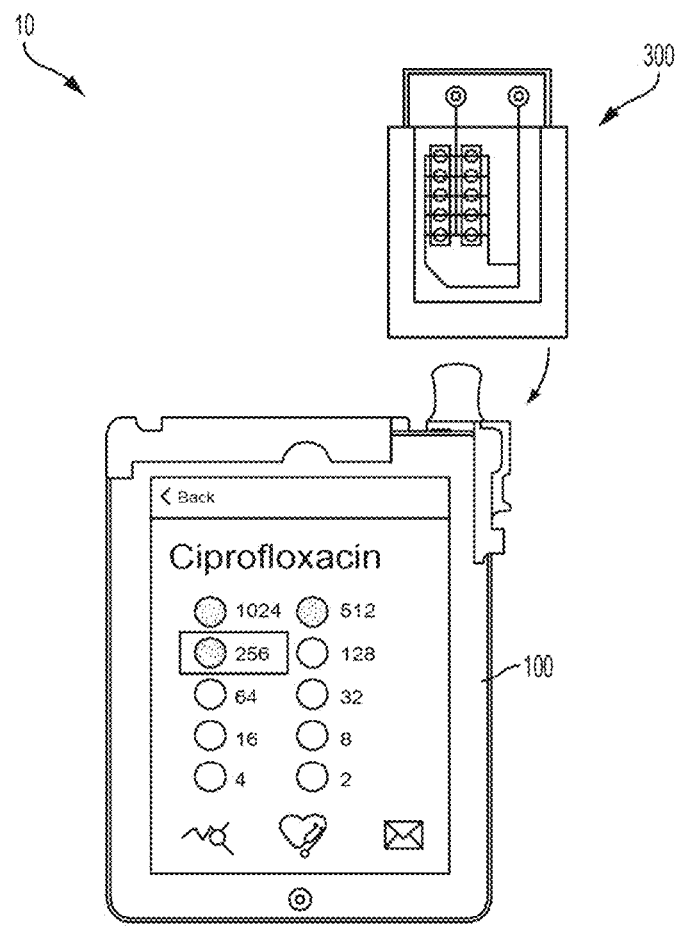
FIG. 8 is a perspective view schematic representation of an exemplary embodiment of the MIC chip in the device.

Referring now to FIG. 8, there is shown a perspective view schematic representation of an exemplary embodiment of the MIC chip assembly in the device. In the embodiment of the system 10 shown in FIG. 8, the MIC chip assembly 300 can be inserted into a second port on the device 100. For example, the MIC chip assembly may be inserted into a port on an electronic device, such as a smartphone. The integration of the MIC chip assembly 300 into the device 100 is critical for interpreting colorimetric results that may not be interpreted efficiently by eyesight. It is contemplated that the device 100 may comprise a digital camera, sensor, or other imaging mechanism that can capture the colorimetric result produced in the wells 306 and transmit data indicating the results to a processor in device 100. An imaging mechanism of the device 100 will allow the device 100 to interpret the minimum inhibitory concentration, which is the lowest concentration where no significant color change is shown.

Figure 9:
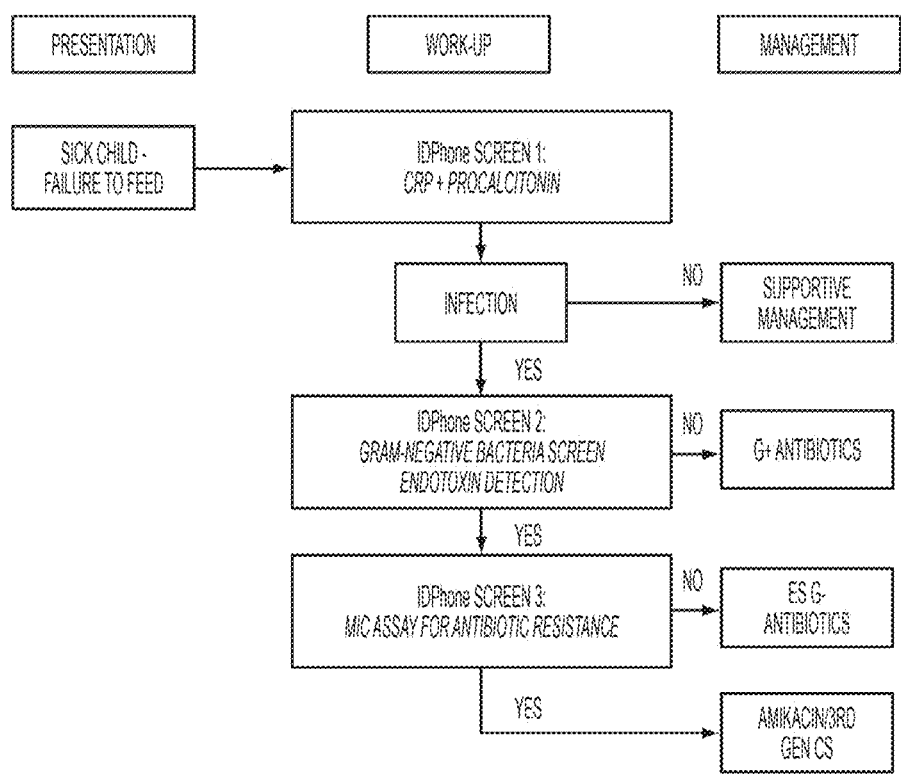
FIG. 9 is a flowchart illustrating a method for diagnosing neonatal sepsis and determining the appropriate treatment.

Referring now to FIG. 9, there is shown a flowchart illustrating the method for diagnosing neonatal sepsis and determining the appropriate treatment. The flowchart shown in FIG. 9 is exemplary of one embodiment wherein the targets are C-Reactive Protein (CRP), procalcitonin (PCT) and Endotoxin. At the first step, the system 10 as shown in FIG. 1, detects the presence of a bacterial infection. At this step, lateral flow assays are conducted in the fluid network 200 to detect Endotoxin, CRP, and PCT. The CRP and PCT assays are analyzed first as CRP and PCT have been shown to have high sensitivity and specificity in this context. If neither CRP nor PCT is detected, supportive management is recommended. Next, the Endotoxin assay is analyzed to determine if the bacterial infection is due to gram-negative bacterium. If Endotoxin is detected, gram-positive antibodies are recommended for treatment. Finally, the system 10 will determine whether the gram-negative bacterium causing the infection is sensitive to first-line antibiotics. This step occurs using the MIC assay in the MIC chip assembly 300. Once antibiotic sensitivity is assessed, the proper antibiotics can be administered. This method can be conducted rapidly at the point-of-care using the system 10 shown in FIG. 1 and explained in detail above.

According to an embodiment is a method and assay for detecting antibiotic resistance and antibiotic resistance markers in *Neisseria gonorrhoeae* (NG). Current CDC estimates indicate 820,000 new NG infections in the United States alone every year. NG has progressively developed resistance or decreased susceptibility to multiple classes of antibiotics, including penicillins, sulphonamides, tetracyclines, quinolones, macrolides and cephalosporins. Early determination of antibiotic susceptibility, ideally at the point of care, to enable appropriate personalized prescription of antibiotics is critical to preserve the curable nature of this infection. Nucleic acid amplification tests (NAATs) are currently used to identify NG from clinical specimens with several manufacturers now offering commercially available and FDA-cleared NAAT assay platforms for the detection of *Chlamydia trachomatis* and NG in the United States. However, antibiotic susceptibility testing is still dependent on culture, which is labor-intensive and time-consuming, and only available at limited number of reference laboratories and some hospitals nationwide.

According to an embodiment, a sample is collected for analysis. The sample can be obtained from a person or any other source. For example, the sample may be a urogenital sample, although any other sample capable of and/or suspected of NG may be utilized. Referring to FIG. 6, for example, a sample 310 is mixed with a biorecognition element 312 to create a mixture 314, and the mixture 314 is then inserted into an inlet 316 on the MIC chip 304. In this embodiment, bis-Zn-DPA functionalized magnetic nanoparticles specific to NG are mixed with the sample, and the NG bacteria attach to the nanoparticles. The NG organisms that bind to magnetic nanoparticles are captured at the MIC well sites and exposed to different concentrations of antibiotics. Colorimetric results interpreted by camera and output to the user.

The first step is to identify and extract the NG organism from the sample. According to an embodiment, magnetic nanoparticles functionalized with capture ligands specific to gram negative or gram positive bacterial organisms are mixed with the sample. Capture ligands have been previously demonstrated including recent synthetic ligands (e.g. bis-Zn-DPA) which can reduce the time required. During an incubation step these nanoparticles attach to the bacterial organisms in solution through this binding interaction, the speed of which can be enhanced through external mixing.

According to an embodiment, validation can be performed by doping healthy urine samples with *E. faecalis* and *E. coli* organisms (as representative gram negative and gram positive organisms) at concentrations ranging over the expected physiological range. A prototype MIC chip can be constructed to evaluate the capture efficiency of the method at the well sites, while varying the flow rates, nanoparticle concentration, and/or binding ligands to obtain the optimal performance. While capture efficiency with a fixed period of time can be a metric of success, these experiments will also enable a determination of the concentration limit of detection (capture). Magnetic bead methods have enabled capture and detection of organisms down to 10 cfu/mL. Preliminary calculations suggest that an initial concentration of organisms at $2\times10^2$ cfu/mL (from a 3 mL sample) will be sufficient to provide MIC information on several different antibiotics, which is above the likely capture cut-off and within the clinical range.

To develop and/or test an assay for NG, healthy urogenital samples doped with NG organisms at concentrations ranging over the expected physiological range can be utilized. Male and female urogenital specimens can be seeded with the NG isolates, including MDRO isolates. The isolates have AST data, including actual MIC values and categorical interpretations. A MIC chip can be constructed to evaluate the capture efficiency of the method at the well sites, varying the flow rates, nanoparticle concentration, and binding ligands to obtain the optimal performance.

According to an embodiment for NG detection, an operator can collect a urogenital sample (via sterile swab), and inserts this into a buffer-containing compartment as shown in step 1 of FIG. 6. After approximately 10 minutes the swab is removed, the compartment is closed, and the sample and buffer are forced through the membrane thereby mixing the sample with the buffer. Next, a traditional magnetic bead separation approach is utilized. Magnetic nanoparticles functionalized with capture ligands specific to NG are mixed with the sample. Numerous capture ligands have been previously demonstrated including recent synthetic ligands (e.g. bis-Zn-DPA) which can reduce the time required. During an incubation step these nanoparticles attach to the NG organisms in solution through this binding interaction, the speed of which can be enhanced through external mixing.

The next step is a MIC assay. Accordingly, the system comprises a MIC assay chip for performing the colorimetric antibiotic susceptibility assay. According to an embodiment, the chip can be manufactured using PMMM-type microfluidic manufacturing techniques, although other methods and materials are possible. The chip can comprise, for example, well sites prefunctionalized with hydrogel pads containing antibiotic doses. According to the embodiment for NG detection, following the bacteria/nanoparticle binding step the urogenital sample and nanoparticle mixture is drawn from the container and inserted into the MIC chip, where the organisms are separated from the urogenital sample by magnets located at the well sites and culture media containing glucose and the pH indicator (phenol red) is provided. Because each well contains a different initial antibiotic concentration, some wells will change color, indicating that the antibiotic concentration is insufficient to kill the NG organism, which still remains active and can produce acid from glucose. Wells that do not change color for the embodiment shown indicate that the level of antibiotic was sufficient to kill or reduce the activity of the NG organism. The lowest concentration that does not show a significant color change is the MIC value. According to an embodiment, preliminary results are provided in approximately 1 hour or less form sample application.

Similarly to the NG development and testing, the system can be tested, optimized, and/or utilized with model organisms, such as appropriate strains of *E. faecalis, P. mirabilis, K pneumoniae*, and *E. coli*, among others, and antibiotics such as vancomycin, tetracycline, and kanamycin, among others. During initial development phases the organisms can first be spiked in human urine and results obtained compared with standard MIC assays. Bacterial concentrations used in these experiments can be consistent with a range of separable concentrations obtained from previous results to ensure that when both methods are combined they will be likely to work.

According to an embodiment, a series of validation experiments can be performed against collected human samples. A subset of the collected shown to be positive for bacterial infection will be tested in both the MIC chip and sent for standard ABR testing at the same clinical laboratory used to perform A validation analysis. These samples will be challenged against a similar set of antibiotics used to do the traditional ABR analysis in the MIC chip and the results compared. Once validation is complete, a pilot validation can be performed comprising a number of blind samples taken from a first batch of samples obtained from a partner such as a hospital. The main metrics for comparison will be accuracy against the gold standard and final time to result.

One challenge of the MIC chip assay is the capture of sufficiently high numbers of organisms from the urine sample using the magnetic nanoparticle approach proposed. While nanoparticle approaches have been previously demonstrated, the relatively low concentration of organisms in urine makes this a challenge. Accordingly, one or more additional pre-processing steps may be necessary to concentrate the organisms. The procedure(s) may include, for example, a preliminary centrifugation and one or more washing steps. Although this may increase the amount of time required to perform the test and obtain the final result or a reduction in the fidelity of the results, a result will still be obtained significantly faster than the state of the art.

Figure 10:
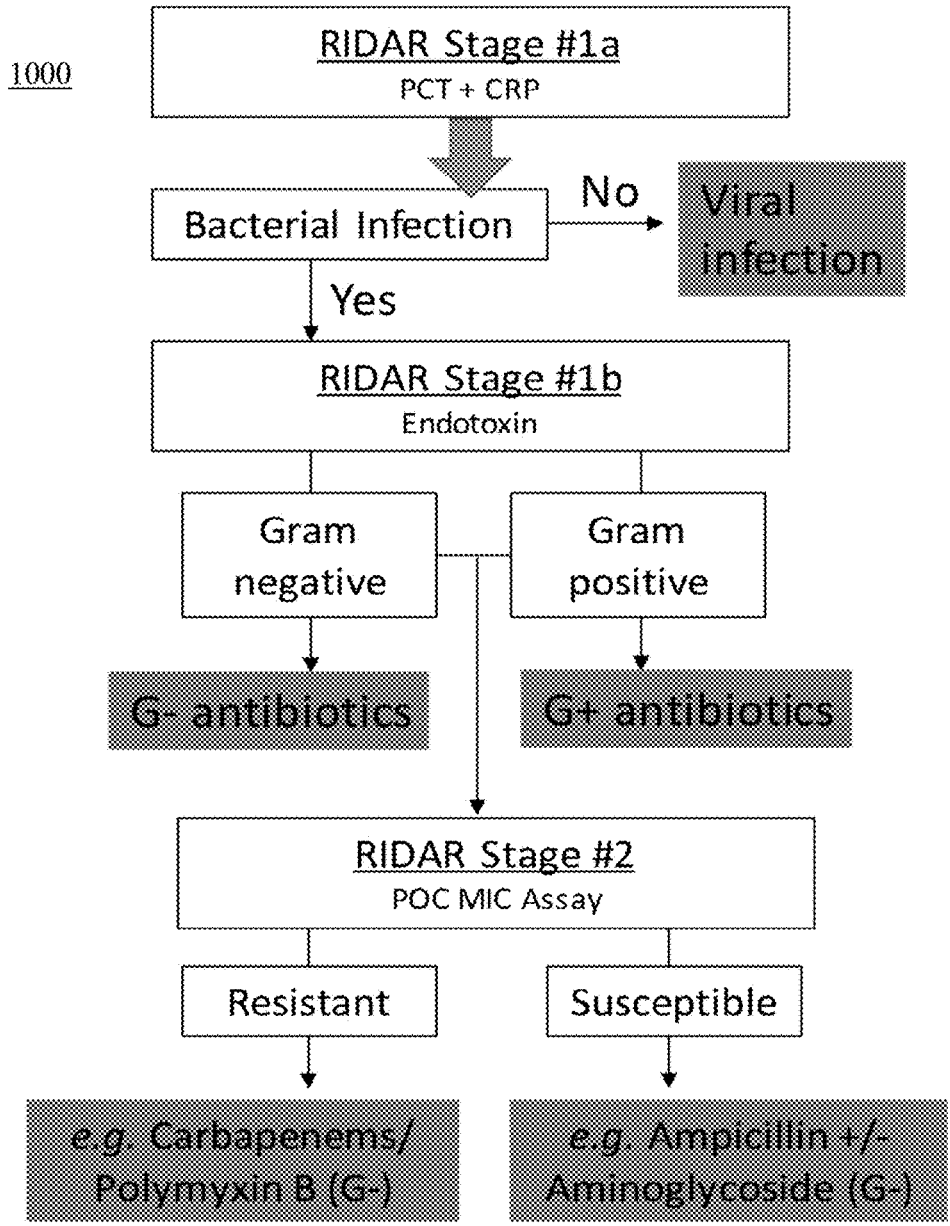
FIG. 10 is a flowchart of a method for rapid identification of infection diseases and antibiotic resistance.

Referring to FIG. 10, in one embodiment, is a flowchart of a method 1000 for rapid identification of infection diseases and antibiotic resistance, similar to the method of FIG. 9. According to an embodiment, the assay enables point-of-care discrimination between gram positive, gram negative, and viral infections in about 10 minutes and provide antibiotic susceptibility information in about 1 hour. The analytical process flow for the assay is shown in FIG. 10, noting that the assay can be deployed as two separate tests if desired. According to an embodiment, the resistant bacteria captured at hospitals may include, for example, vancomycin-resistant enterococci (VRE). Notably, samples may include urine samples, urinary tract infections, saliva, blood, and many other sources.

According to an embodiment, the first stage of the test comprises a 3-plex test that screens for C-Reactive Protein (CRP) and Procalcitonin (PCT) levels in blood and endotoxin (ENDO) levels in urine. According to an embodiment, the test is composed of one or two plastic cartridges that house the lateral flow type assays for CRP & PCT (combined in one test) and endotoxin. Several biomarkers have been used to determine the presence of infection, particularly in the context of sepsis. The two most commonly used biomarkers are the acute phase protein CRP and PCT. CRP is produced in the liver and typically released in the 24 hours after the onset of inflammation or tissue damage. CRP has been used to differentiate bacterial and viral infections in earlier studies and has demonstrated moderate to high sensitivity and specificity for detecting the likelihood of infections and sepsis. PCT is the prohormone of calcitonin and is produced extensively in response to mediators and cytokines released in response to bacterial infections, such as TNF-alpha and IL-6. It has also been shown to strongly correlate with the extent and severity of bacterial infections. PCT levels increase within 4 to 12 hours upon stimulation and circulating PCT levels drop by 50% per day when the infection is controlled. Recent literature meta-reviews have shown average sensitivity and specificity of CRP in determining bacterial infections was 67% and 86% and PCT was 85 and 83% in different population groups. However, the sensitivity and specificity of determining bacterial infections are significantly improved by combining the two tests. Endotoxin or lipopolysaccharides (LPS) are found in the outer membrane of gram-negative bacteria and thus detection of levels of the toxin in urine is indicative of a gram-negative urinary tract infection. A comparison of the sensitivity and specificity of CRP and PCT in detecting bacterial infections is shown in TABLE 1.

TABLE 1

Comparison of sensitivity and specificity of CRP and PCT in detecting bacterial infections.

| Outcome | Biomarker | Cut-off range | Sensitivity (%) | Specificity (%) |
|---|---|---|---|---|
| Bacterial Infection | CRP | 6-100 mg/L | 78 | 60 |
| | PCT | 0.5-6.1 ng/mL | 85 | 83 |

It is expected that using both biomarkers improves the overall sensitivity and specificity for detecting bacterial infection. Further, by using both, infections will not be missed, particularly early on, that will be missed if only using CRP. This combination should help determine when to start and/or when to stop antibiotics. The final cut-off value uses in the diagnostics can be determined during experimentation, however it is expected that the values will be around 1 ng/mL for PCT and 20 mg/mL for CRP, although other values are possible. Endotoxin or lipopolysaccharides (LPS) are found in the outer membrane of gram-negative bacteria and thus detection of circulating levels of the toxin is indicative of a gram-negative bacterial infection. There have been several recent technical developments whereby the detection of endotoxin has been used to help diagnose the causative agent behind infections, including urinary tract infections. The levels of circulating endotoxin depend on the severity of the injection but detection in the 1 ng/mL range would be indicative of the nature of the infection. Accordingly, by adding Endotoxin detection following the PCT/CRP screen, the choice of antibiotics is further refined.

As shown in the FIG. 10 flowchart, the combined levels of PCT and CRP allow one to discriminate between bacterial and viral infections and the ENDO levels allow further discrimination between gram positive and gram negative bacteria. Based on preliminary data, it is expected that this stage can be complete in about 10 minutes. The second stage comprises a point-of-care minimum inhibitory concentration (MIC) assessment of the bacterial infection against common antibiotics. It is expected that the second stage MIC assay can report accurate results in about 1 hour or less and, when combined with the more rapid broad information from stage 1, significantly improves antibiotic selection and stewardship. The system can be validated using a variety of microorganisms, including but not limited to *E. faecalis, P. mirabilis, K pneumoniae, E. coli*, and/or vancomycin-resistant enterococci.

According to an embodiment, to operate the CRP/PCT test, a user applies a drop of blood onto a filtration membrane, which is incorporated into the assay strip. The user then applies buffer droplets onto the buffer inlet that initiates the plasma to flow to the test and control line areas. In parallel, the ENDO cartridge is dipped in a urine sample and the wicking stricture uptakes the sample and moves it towards the lateral flow assay. Following completion of the test, a signal enhancement technique is used for PCT and Endotoxin which are found in very low concentrations (pg/ml-ng/ml) in blood/urine but not for CRP for which the detection range is higher (μg/ml) and allows the detection without the enhancement. The CRP version of the test has been demonstrated and validated through human trials and the cartridge reader system has been developed. Based on these data, it is expected that this stage could be complete in as little as 10 minutes or less.

Following stage 1 of the screen, and depending on the results, it may be useful to perform an antibiotic resistance assay in order to optimize antibiotic administration. It is noted however that this is an "add-on" to the first stage assay, which in and of itself has value in antibiotic stewardship. Stage 2 of the assay is designed as a point-of-care test to be used as necessary. Briefly, according to one embodiment, magnetic nanoparticles functionalized with capture ligands specific to bacterial organisms (specifically bis-Zn-DPA functionalized magnetic nanoparticles) are mixed with the urine sample. During a mixing step, these nanoparticles attach to the bacterial organisms in solution through this specific interaction. The mixture is then drawn from the container and inserted into the MIC chip.

Figure 11:
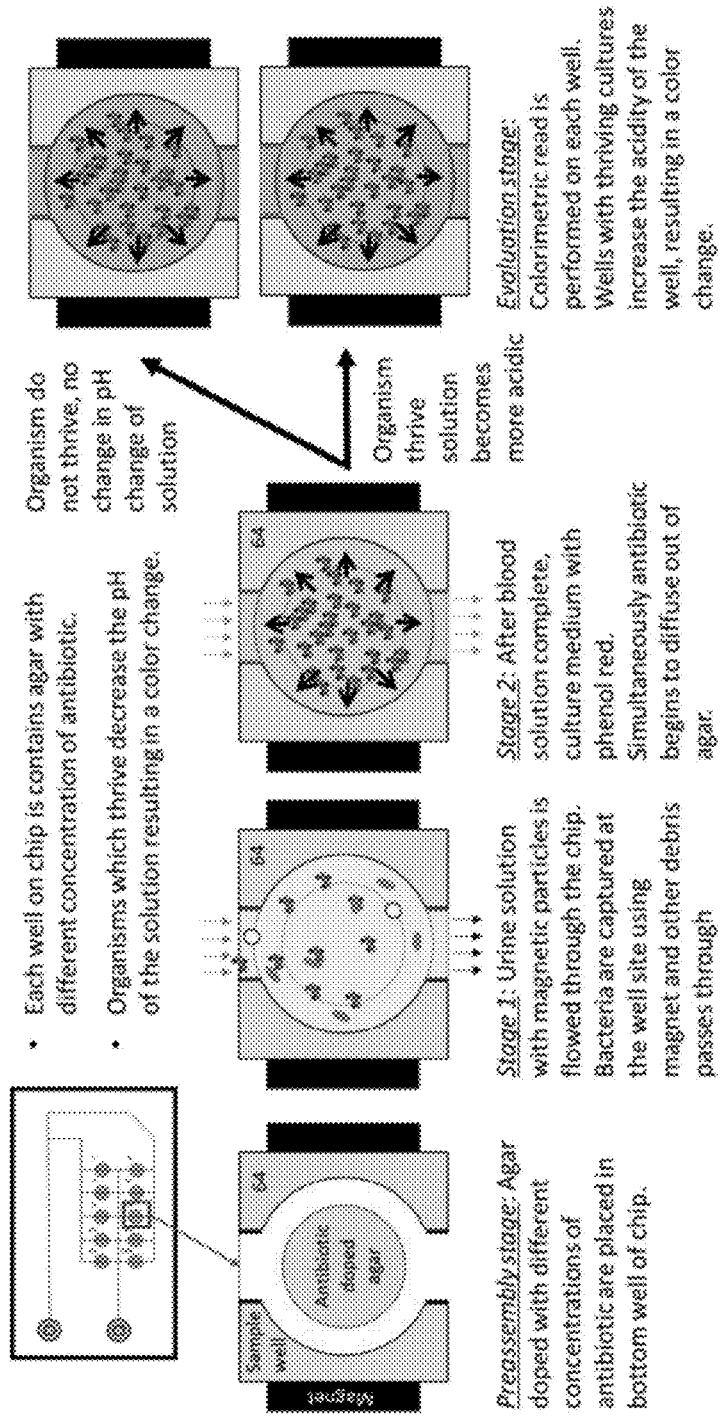
FIG. 11 is a diagram of an exemplary embodiment of a well during a MIC assay.

Details of the operation of an embodiment of the MIC chip assay are shown FIG. 11. As can be seen in these images, the MIC chip contains a series of prefunctionalized wells with specific concentrations of an antibiotic within a solid media (specifically doped agar). The MIC chip is inserted into the "Chip Interface" attached to a reader which contains magnets that align with the well array. After insertion, the sample is flown through the chip in such a way that the sample is evenly distributed to each of the well sites. Because the magnets are located there the organisms attached to the bacteria will remain in the wells while any other material in the sample will flow through. After the sample is inserted, culture medium with an indicator is flown into the MIC chip. This serves to wash out the remainder of the sample but also introduce growth/culture medium and the chemical indicator. This chemical indicator is phenol red, for example, which will change the color of the solution in the presence of metabolically active organisms as their metabolic activity changes the pH of the solution. Because each of the wells is has a different initial antibiotic concentration, some wells will change color indicating that the concentration of antibiotics is not sufficient to limit growth the organism. Wells that do not change color indicate that the level of antibiotics was sufficient to kill or reduce the activity of the organism. This colorimetric result can be interpreted by eye, or quantitatively interpreted. The lowest concentration that does not show a significant color change is the minimum inhibitory concentration. One goal for this assay is to provide preliminary results in about 1 hour from when the sample is taken.

Figure 12:
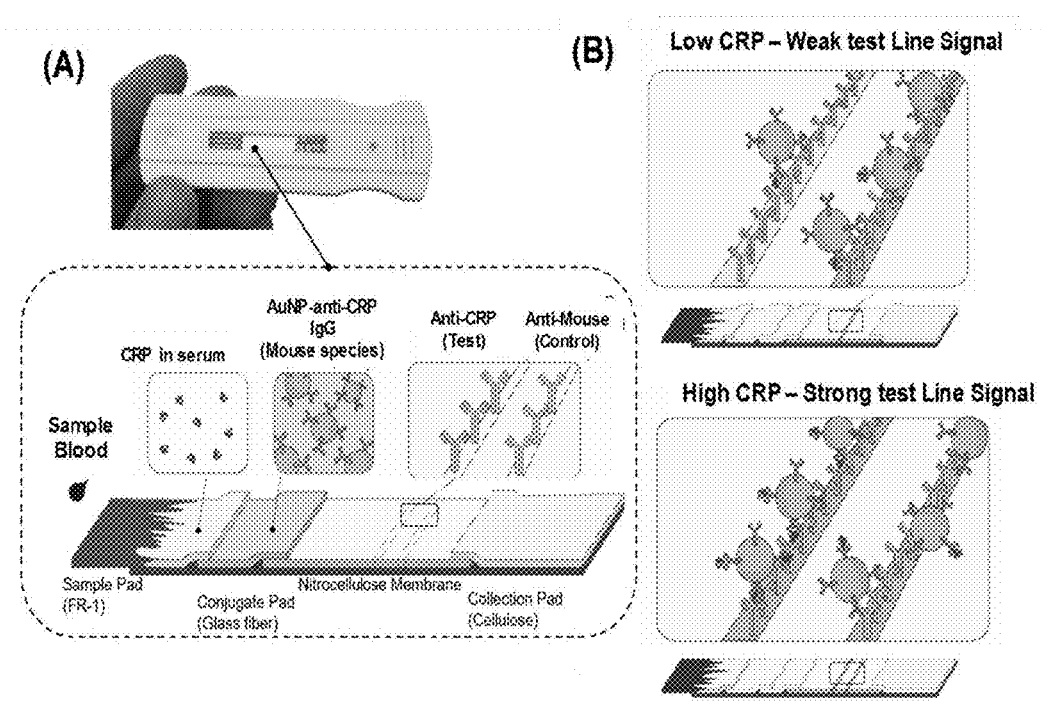
FIG. 12 is a diagram of an exemplary embodiment of a C-Reactive Protein (CRP) assay.

Referring to FIG. 12 is an embodiment of a CRP assay. FIG. 12A is a schematic representation of a strip image and schematic of a custom CRP test strip architecture and components, FIG. 12B is a schematic representation of sandwich interaction results in a weak T/C signal intensity for low CRP in the sample, and FIG. 12C is a schematic representation of a strong T/C signal intensity for high CRP in the sample.

Figure 13A:
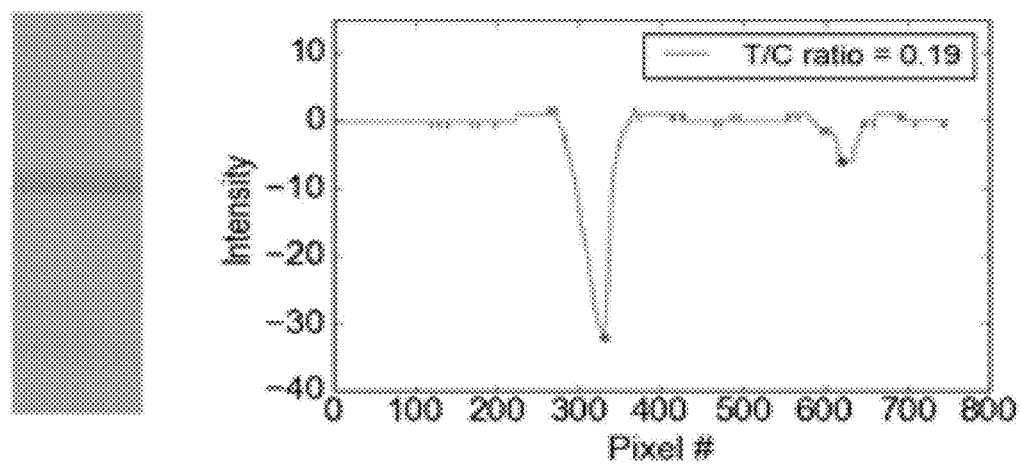
FIG. 13A is a graph of results of an exemplary embodiment of a CRP assay.
Figure 13B:
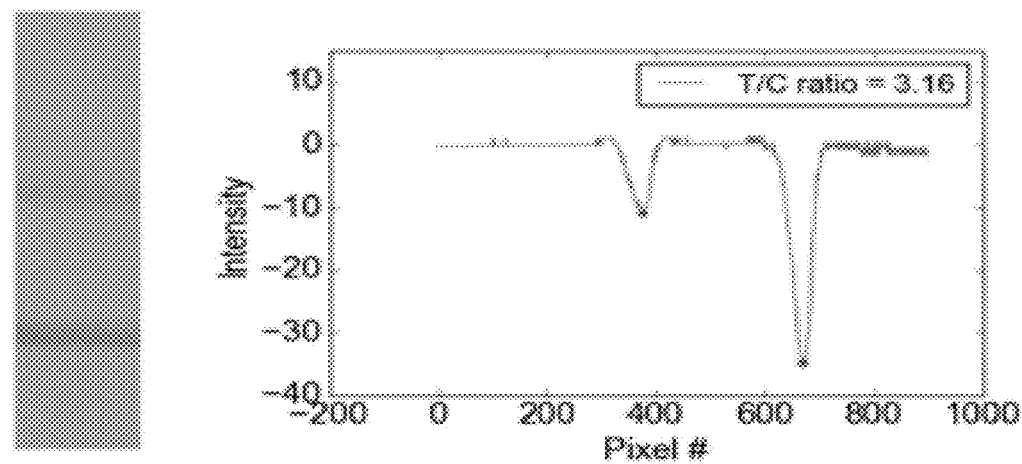
FIG. 13B is a graph of results of an exemplary embodiment of a CRP assay.
Figure 13C:
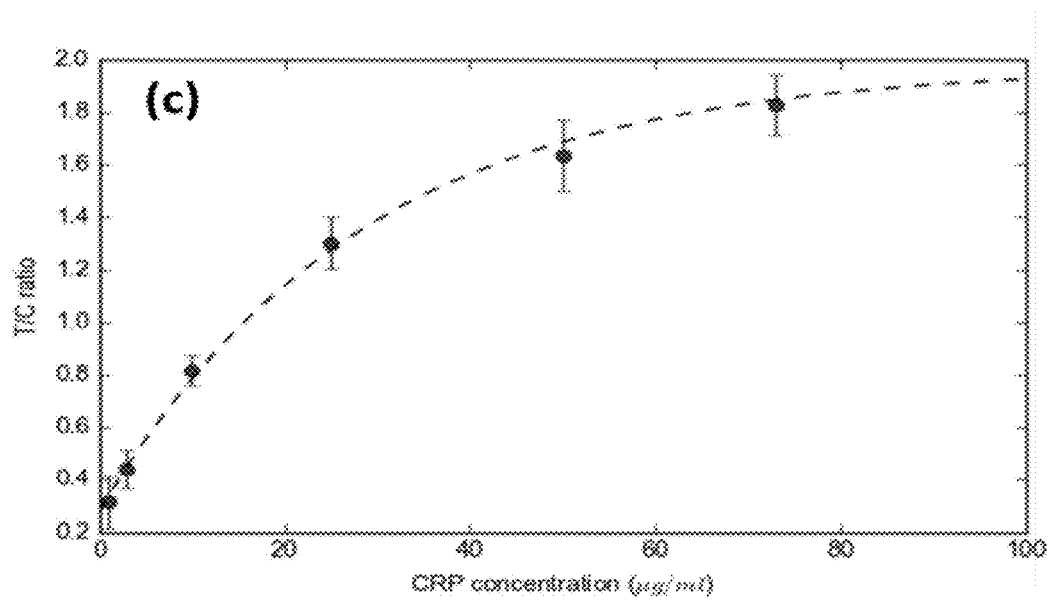
FIG. 13C is a graph of results of an exemplary embodiment of a CRP assay.

As shown in FIG. 12, according to an embodiment, the assay takes a lateral flow format starting with the addition of a finger stick of blood and chase buffer added to the blood filtration pad. This removes the removes the red blood cells from the sample and drives the serum sample to the conjugate pad where it mixes with the mouse anti-CRP IgG conjugated gold nanoparticles. The sample then continues to mix (enabling the free CRP to bind to the nanoparticles) as it is further wicked downstream until it reaches the test and control lines. As with other sandwich type assays, a secondary antibody at the test line captures the gold nanoparticles with CRP bound to them and the control line captures the remainder which pass by. As shown in FIG. 13B a low concentration of CRP in the sample tends to result in few nanoparticles on the test line (compared with the control) and a higher concentration of CRP results in more. The system allows one to read the intensities of these control lines and use their relative ratios to quantify the levels of CRP. FIGS. 13A and B show example high/low results for the CRP assay and FIG. 13C demonstrates the ability to quantify results over the 0 to 100 µg/mL range.

Figure 13D:
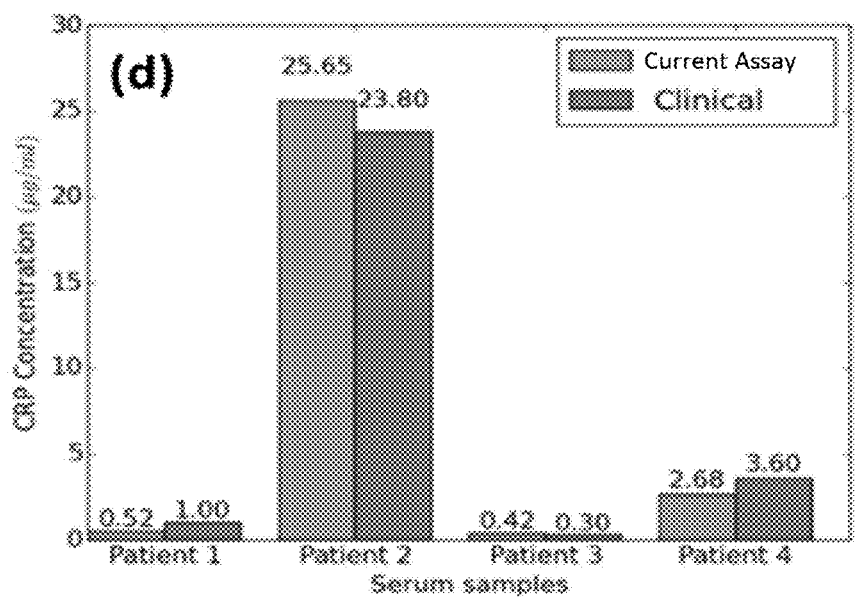
FIG. 13D is a graph of results of an exemplary embodiment of a CRP assay.

The system was also validated clinically in serum samples. Four serum samples were collected from clinical patients with rheumatoid arthritis, which were measured with the hardware shown above and with a standard clinical assay for comparison. From the comparison results shown in FIG. 13D, the maximum error and average inter-sample difference were 1.85 µg/mL and 0.85 µg/mL, respectively. As shown in FIG. 13D, both the current assay and the clinical assay agree that two patients have normal CRP, one has elevated CRP, and one has high CRP consistent with a rheumatoid arthritis flare-up. These results show the viability of the approach for quantitative, point-of-care CRP monitoring.

Figure 14:
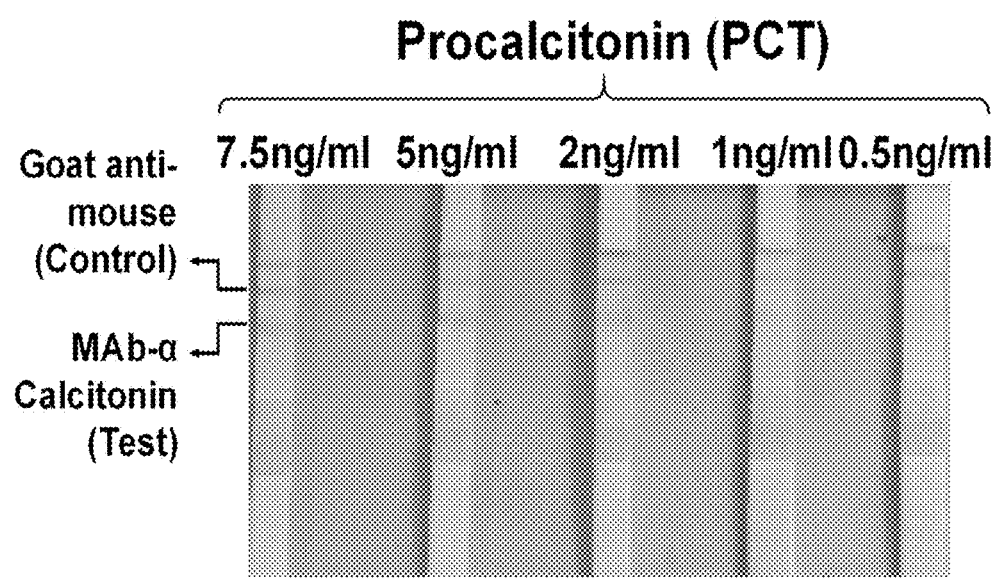
FIG. 14 is a representation of results of an exemplary embodiment of a procalcitonin (PCT) test.

In addition to the CRP test, a PCT test using the same format was developed. As shown in FIG. 14, the lateral flow strip was prepared by immobilizing of mouse monoclonal antibody anti-Calcitonin/Ab2 (0.5 mg/ml) on the test line of LF strip, and Goat anti mouse (0.35 mg/ml) on the control line. The strips were incubated overnight at 37° C. To test the strips, another mouse monoclonal antibody anti-PCT/Ab1 (0.2 mg/ml) previously conjugated with 40 nm gold nanoparticles was deposed in the conjugated pad, and allowed to dry for 5 minutes. A tube containing 10 µg of lyophilized Procalcitonin (PCT) antigen was re-suspended in 1×PBS to get a working solution of 0.1 mg/ml (100 ng/ml). From this solution, several dilutions were prepared in 1×PBS to get PCT concentration of 7.5 ng/ml, 5 ng/ml, and 2 ng/m, 1 ng/m, and 0.5 ng/ml. Ten microliters (10 µl) of diluted PCTs were then used as samples in a LF assay, and running buffer added to the strip to allow capillarity migration. As can be seen in FIG. 14, good discrimination of the results was obtained over the range of interest (see Table 1).

The test strips for CRP, PCT and Endotoxin can be based on sandwich-type lateral flow principles. The detectable target (CRP, PCT or Endotoxin) of the assay is determined by the choices of the detection and capture antibodies (anti-CRP, anti-PCT or anti-Endotoxin) during the assay development. As with the aforementioned tests, the main components of the test strip can be, for example, a conjugate pad that stores the gold nanoparticle-labeled detection antibody, detection pad that immobilizes the capture antibody for the corresponding target, and a control pad that immobilizes the secondary antibody with an affinity for the common species (e.g. mouse, rabbit, goat etc.) of the detection antibodies. The main difference between the two assays is that the PCT/CRP test can be a single multiplexed test along a single lateral flow strip (i.e. two test lines, one for PCT and one for CRP) and the ENDO assay can use the urine packaging shown or otherwise envisioned herein, according to one embodiment.

According to an embodiment, the sample flows downstream via capillary action and mixes with the detection antibodies on the conjugate pad. The detection antibodies interact with the target CRP, PCT or Endotoxin molecules if present in the sample and form a target-to-antibody complex. When transported over the detection pad, only the target-to-antibody complexes are captured by the capture antibodies which have the affinity towards the corresponding targets but not the detection antibodies alone. The unreacted detection antibodies flow further downstream and be captured by the secondary antibodies on the control pad. As a result, the detection band will turn increasingly darker for higher concentration of the target molecules in the sample as this will result in more target-to-antibody complexes that are captured. When the target concentration is low, the detection band will exhibit only a subtle change, while there will be a distinctly visible signal on the control pad. Quantification can be done using one or more of the methodologies described above and validated for human samples.

Any additional validation and reagent optimization can be done using spiked buffer solutions over the range of expected physiological concentrations. The strips can be designed to centralize the range of quantification based on the diagnostic cut-offs described in Table 1. Once complete anonymized human serum and urine samples can be analyzed. CRP, PCT and ENDO concentrations in these samples can be characterized using standard ELISA and then used to develop the calibration curve for the test strips. The human sample method can be utilized to calibrate the strips rather than the buffers as the different flow conditions in the strip can affect the final test-line development. Final engineering specifications for the strips can include, for example, time to result, dynamic range, and limit of detection. Following development of the calibration curve a set of diagnostic assays can be performed using blind human samples. From these samples the final test accuracy and error can be determined as well as the clinical sensitivity and specificity. The number of samples will be consistent with statistical power requirements.

According to an embodiment, additional assay instruments can be designed, constructed, and utilized. The assay instrument can, for example, be compatible with the two-stage assay. The design of the assay instruments may include, for example, a wider imaging field to enable imaging of the entire cartridge. Quantification of reaction results may be performed using a wireless interface, which allows repeatable image analysis of any size test strip while eliminating the possibility of contaminating the smart device being used for the analysis.

According to an embodiment, the assay instrument can be opaque, and all hardware components can be enclosed within it, which blocks the influence of external lighting. Its small size and battery-powered operation also make it conveniently portable and easy to use in remote or resource-limited settings. The flexibility of the device allows different cassette formats from diverse manufacturers to be used, reducing the amount of reengineering that will have to be done here. The device is controlled via wireless connectivity with the smart device that is running the application. The user is first instructed to insert the test cartridge into a pullout tray that slides into the device and eliminates any ambient light. Batteries in the base of the device power the components, eliminating the need to connect to a power source. A green indicator LED on the outside of the device will show the user that it is powered on. A camera is fixed at a specific height above the strip that allows for the optimum focal length to be achieved. A ring of LEDs surrounding the camera lens mimics a ring flash, like that used in macro photography. This light setup provides uniform illumination of the test strip without creating shadows. Colored indicator LEDs on the outside of the device will provide feedback on the analysis progress. First, a red and subsequent yellow LED will indicate that the necessary time for strip development is passing. After the strip has developed, a command is sent to the device to turn on the inner LED ring and take an image of the inserted test strip. The green indicator LED is lit after the image is taken. The acquired image is returned to the smart device, and the software executes several steps to determine the result before displaying it on the screen. This description is for one possible embodiment, and many modifications and alterations from this description are possible.

Example—Dual Lateral Flow Assay for Detection of C-Reactive Protein and Procalcitonin According to an embodiment is a dual Lateral Flow (LF) assay for Point-Of-Care detection of one or more biomarkers of sepsis and/or systemic inflammation, for example. C-Reactive Protein (CRP) and Procalcitonin (PCT) are examples of biomarkers of sepsis and systemic inflammation. The concentrations of these two proteins generally increase several fold in the host during a bacterial infection, resulting in their use in clinical settings as biomarkers for diagnostic of systemic inflammation and sepsis.

Figure 15A:
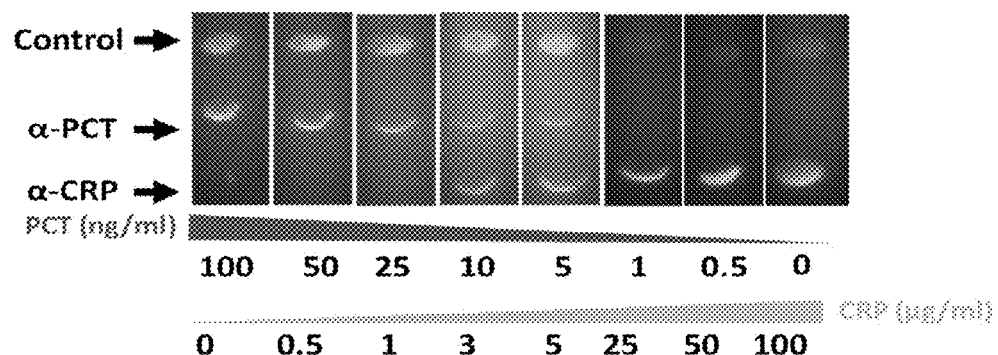
FIG. 15A is a representation of results of an exemplary embodiment of a dual lateral flow assay for detection of CRP and PCT.
Figure 15B:
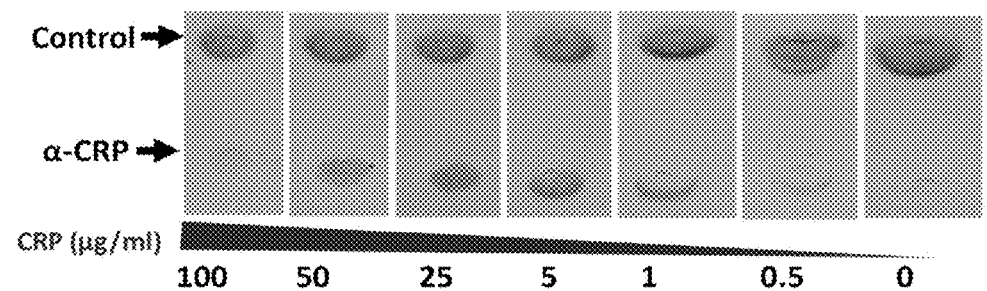
FIG. 15B is a representation of results of an exemplary embodiment of a lateral flow assay for detection of CRP.
Figure 15C:
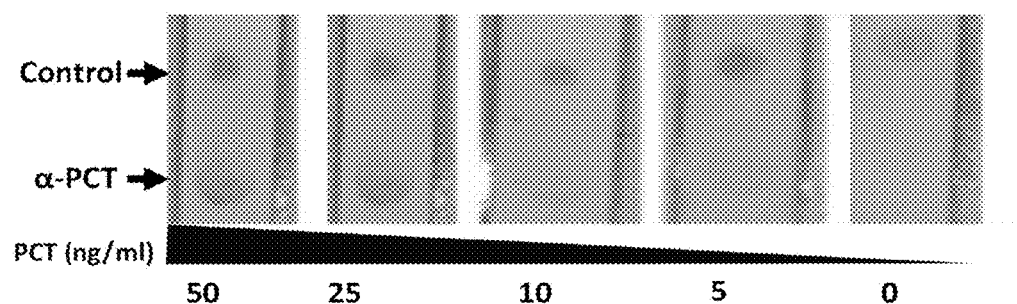
FIG. 15C is a representation of results of an exemplary embodiment of a lateral flow assay for detection of PCT.

According to an embodiment, detection antibodies are utilized against PCT and CRP conjugated to either Fluorophores or 400 nm latex bead particles to detect these biomarkers with greater sensitivity levels on a LF test trip containing immobilized corresponding capture antibodies. Referring to FIGS. 15A-15C, for example, are the results of LF assays. FIG. 15A shows the results of a dual CRP-PCT LF assay using fluorophore conjugates, FIG. 15B shows the results of a CRP LF assay using a red latex bead conjugate, and FIG. 15C shows the results of a PCT LF assay using blue latex bead conjugate.

According to an embodiment, the sensitivity level of detection may be configured to be at or near the 10 pg/ml range to account for the scarcity level of this biomarker in sera of healthy individuals. Accordingly, other particles, including but not limited to Europium particles, which have been shown to be thousand-fold more potent than current particles, may be utilized. A UV transilluminator UV reader may be used for detection of these particles.

Example—Antibiotic Susceptibility Testing

Figure 16:
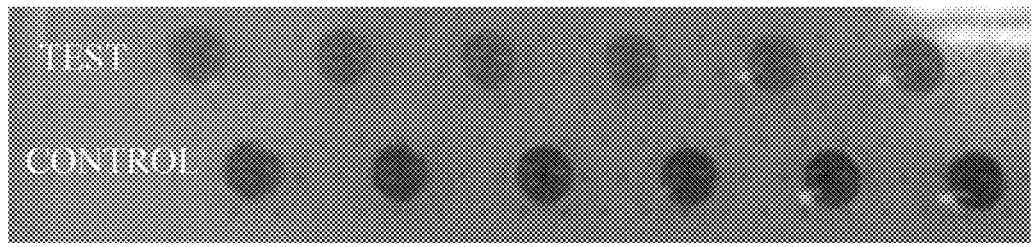
FIG. 16 is a representation of results of an exemplary embodiment of a colorimetric phenotypic test.

According to an embodiment, a colorimetric phenotypic testing approach was utilized to assess the antibiotic susceptibility of an attenuated *E. coli* K12 strain. The pH indicator phenol red was used to provide a phenotypic indication of bacterial growth. For colorimetric phenotypic testing approach, bacterial growth tests were conducted with small sample volumes in a PDMS microchip. The *E. coli* strain with a kanamycin resistance gene as a selection marker was first streaked and incubated overnight on LB agar plates containing kanamycin. Single colonies were subsequently picked and propagated in liquid bulk culture. Following overnight bulk culture to stationary phase, small volumes (~1 µL) of culture were separately incubated on the PDMS chip in wells each containing a 19 µL mixture of fresh LB media, 0.05% phenol red, and the antibiotics kanamycin (control) and ampicillin (test). The metabolic activity of viable bacteria leads to an accumulation of organic acids in the growth media, which causes the phenol red to change in color from red to yellow, which is expected for the control group as the *E. coli* stain is kanamycin resistant. Images of the chip were taken every hour, and a significant color change was detected after 4 hours, as seen in FIG. 16.

A similar experiment was conducted by incubating the bacteria culture in capillary tubes designed to hold microliters of liquid. It was hypothesized that the increased surface area to volume ratio of the tubes would induce an accelerated growth rate for the bacteria. First, an overnight experiment was conducted to verify that incubation inside capillary tubes supported bacteria growth. Following this verification experiment, a shorter timescale experiment was conducted with added antibiotics. Similar to the previous experiment, a significant color change was detected in the control group (kanamycin) at the 4-hour mark. No color change was observed in an ampicillin inhibited group.

While embodiments of the present invention have been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements, it will be understood that the exemplary embodiments can be practiced utilizing either less than or more than the certain number of elements.

What is claimed is:

1. A method for detecting the presence of a target in a sample, comprising the steps of:
providing a device having a first port configured to receive a multi-layered substrate having a sample inlet and a reagent inlet, wherein the sample inlet is connected to a first microfluidic channel and the reagent inlet is connected to both the first microfluidic channel and a second microfluidic channel, and further wherein the second microfluidic channel comprises a longer pathway than the first microfluidic channel, and further comprising a first test strip and a second test strip each connected to both the first microfluidic channel and the second microfluidic channel, and a third test strip connected only to the first microfluidic channel, wherein each test strip comprising a conjugate section, a detection section, and a collection section; and a second port configured to receive a chip interface, wherein the chip interface has an open volume configured to receive a chip therein;
inserting the chip into the chip interface;
depositing a sample into the device; and
flowing the sample;
wherein the chip is a MIC chip.

2. The method of claim 1, further comprising depositing detection antibodies at the conjugate section, wherein the detection antibodies are labeled with nanoparticles.

3. The method of claim 2, wherein the detection antibodies are conjugated with fluorophores.

4. The method of claim 2, further comprising depositing the secondary antibodies at the conjugate section, wherein the secondary antibodies are labeled with nanoparticles.

5. The method of claim 4, further comprising the steps of:
generating a test line indicative of a concentration of the detection antibodies captured at the detection section; and
generating a control line indicative of a concentration of the secondary antibodies captured at the detection section.

6. The method of claim 1, wherein the device further comprising a software to determine a result before displaying the result on a screen.

7. A method for detecting the presence of a target in a sample, comprising the steps of:
providing a device having a first port configured to receive a multi-layered substrate having a sample inlet and a reagent inlet, wherein the sample inlet is connected to a first microfluidic channel and the reagent inlet is connected to both the first microfluidic channel and a second microfluidic channel, and further wherein the second microfluidic channel comprises a longer pathway than the first microfluidic channel, and further comprising a first test strip and a second test strip each connected to both the first microfluidic channel and the second microfluidic channel, and a third test strip connected only to the first microfluidic channel, wherein each test strip comprising a conjugate section, a detection section, and a collection section; and a second port configured to receive a chip interface, wherein the chip interface has an open volume configured to receive a chip therein;
inserting the chip into the chip interface;
depositing a sample into the device; and
flowing the sample;
wherein the test strips detect the presence of a bacterial infection and whether the bacterial infection is due to gram-negative bacterium; and the chip detects the antibiotic resistance.

8. A method for detecting the presence of a target in a sample, comprising the steps of:
providing a device having a first port configured to receive a multi-layered substrate having a sample inlet and a reagent inlet, wherein the sample inlet is connected to a first microfluidic channel and the reagent inlet is connected to both the first microfluidic channel and a second microfluidic channel, and further wherein the second microfluidic channel comprises a longer pathway than the first microfluidic channel, and further comprising a first test strip and a second test strip each connected to both the first microfluidic channel and the second microfluidic channel, and a third test strip connected only to the first microfluidic channel, wherein each test strip comprising a conjugate section, a detection section, and a collection section; and a second port configured to receive a chip interface, wherein the chip interface has an open volume configured to receive a chip therein;
inserting the chip into the chip interface;
depositing a sample into the device; and
flowing the sample;
wherein the chip comprises one or more wells, and wherein the chip interface comprises one or more magnets that align with the wells when the chip is inserted into the open volume of the chip interface.

9. The method of claim 8, further comprising mixing the sample with a biorecognition element, wherein the biorecognition element is a magnetic nanoparticle functionalized with capture ligands.

10. The method of claim 9, further comprising the step of:
capturing the target in the wells, wherein the target in the sample is magnetically attracted to the magnets in the chip interface.

11. The method of claim 10, further comprising the step of:
growing a culture of the target captured in the wells.

12. The method of claim 11, further comprising the step of:
applying an antibiotic to a solid media in each well.

13. The method of claim 12, wherein each well comprises a different concentration of the antibiotic.

* * * * *